(12) United States Patent
Haschke (10) Patent No.: US 6,986,662 B2
(45) Date of Patent: Jan. 17, 2006

(54) ADHESIVE ENDODONTIC CONES AND RELATED METHODS

(75) Inventor: Erich Haschke, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 111 days.

(21) Appl. No.: 10/410,310

(22) Filed: Apr. 9, 2003

(65) Prior Publication Data

US 2004/0202986 A1    Oct. 14, 2004

(51) Int. Cl.
*A61C 5/00*    (2006.01)
(52) U.S. Cl. .................................... 433/228.1; 433/224
(58) Field of Classification Search ............... 433/224, 433/228.1, 226, 225; 523/116, 118, 117
See application file for complete search history.

(56) References Cited

U.S. PATENT DOCUMENTS

| | | | |
|---|---|---|---|
| 3,925,895 A * | 12/1975 | Kliment et al. ............. | 433/224 |
| 4,100,309 A * | 7/1978 | Micklus et al. ............. | 427/2.28 |
| 4,425,094 A | 1/1984 | Tateosian et al. | |
| 4,931,096 A | 6/1990 | Fujisawa et al. | |
| 4,950,697 A | 8/1990 | Chang et al. | |
| 5,093,130 A * | 3/1992 | Fujii et al. ................... | 424/463 |
| 5,275,562 A | 1/1994 | McSpadden | |
| 5,372,759 A | 12/1994 | Johnson | |
| 5,646,197 A | 7/1997 | Martin | |
| 5,648,403 A | 7/1997 | Martin | |
| 5,856,373 A | 1/1999 | Kaisaki et al. | |
| 6,025,406 A | 2/2000 | Oxman et al. | |
| 6,028,125 A | 2/2000 | Combe et al. | |
| 6,043,295 A | 3/2000 | Oxman et al. | |
| 6,120,294 A | 9/2000 | Engelbrecht et al. | |
| 6,126,446 A | 10/2000 | Mannschedel | |
| 6,187,833 B1 | 2/2001 | Oxman et al. | |
| 6,197,846 B1 | 3/2001 | Combe et al. | |
| 6,220,863 B1 | 4/2001 | Kamohara et al. | |
| 6,472,454 B1 | 10/2002 | Qian | |
| 6,500,004 B2 | 12/2002 | Jensen et al. | |
| 2004/0137404 A1 * | 7/2004 | Koch et al. ................... | 433/81 |

OTHER PUBLICATIONS

"Clinical evaluation of fiber-reinforced epoxy resin posts and cast post and cores"; *American Journal of Dentistry*, (May 2000) 13 (Spec No) 15B-18B; by M. Ferrari, et al.

"A general dentist's viewpoint of two new endodontic techniques"; *Compendium of Continuing Education in Dentistry* (Oct. 1999) 20 (10) 921-4, 926, 928 passim; quiz 934; by D. Seidman.

"The sealing ability of an epoxy resin root canal sealer used with five gutta percha obturation techniques"; *Endodontics and Dental Traumatology*, (Dec. 2000) 16 (6) 291-7; by R. J. De Moor, et al.

(Continued)

*Primary Examiner*—Melba N. Bumgarner
(74) *Attorney, Agent, or Firm*—Workman Nydegger (57) ABSTRACT

An adhesive endodontic cone is chemically compatible with endodontic sealant resins, including hydrophilic resins used for sealing a root canal chamber. The adhesive endodontic cone comprises a hydrophobic elastomer substrate that is sized and shaped so as to be at least partially insertable into an exposed root canal of a tooth. The cone includes an adhesive attached to at least a portion of a surface of the cone so as to render the cone more chemically compatible with a hydrophilic endodontic resin. The adhesive includes a hydrophobic portion that is chemically compatible with the hydrophobic elastomer substrate and a hydrophilic portion that is chemically compatible with a hydrophilic resin.

33 Claims, 4 Drawing Sheets

OTHER PUBLICATIONS

"Adhesion of endodontic sealers to dentin and gutta—percha"; *Journal of Endodontics*, (Oct. 2002) 28 (10) 684-8; by L. Kwang-Won, et al.

"Evaluation of apical sealing of three endodontic sealers"; *International Endodontic Journal*, (Jan. 2000) 33 (1) 25-7; by W. A. De Almeida, et al.

"The long-term sealing ability of an epoxy resin root canal sealer used with five gutta percha obturation techniques"; *International Endodontic Journal*, (Mar. 2002) 35 (3) 275-82; by R. J. De Moor, et al.

* cited by examiner

ADHESIVE ENDODONTIC CONES AND RELATED METHODS

BACKGROUND OF THE INVENTION

1. The Field of the Invention

The present invention relates to the field of dentistry, and more particularly to endodontic cones, such as those made of gutta percha, used in filling root canal chambers.

2. The Relevant Technology

When a dental practitioner performs a root canal, pulp and other material in the root canal chamber is removed. Once a dentist has removed diseased and soft tissue from a tooth's root canal, the chamber must be filled. The purpose of filling the root canal is to seal the area, and to eliminate the possibility of bacterial attraction and infection in the chamber. Filling and sealing the chamber is necessary to prohibit material from draining into the canal, which could attract bacterial contamination of the root canal chamber. In addition, filling the chamber provides a base that may be drilled out later for placement of one or more posts to which may be mounted a crown or other restorative appliance.

The current method of filling the root canal is by inserting a shaped cone of gutta percha into the prepared root canal. Gutta percha typically includes a matrix of trans isoprene, zinc oxide filler, a radiopacifier such as bismuth, barium or strontium, wax or resin, color pigment, plasticizers and other additives.

One difficulty with using gutta percha has been that it does not readily bond to and seal against the tooth tissue. The tooth tissue is quite hydrophilic, while gutta percha itself is extremely hydrophobic. Typical endodontic pastes, used to bond and seal the gutta percha to the tooth tissue, comprise zinc oxide and eugenol. This mixture is hydrophobic, and while it bonds quite well to the gutta percha, its bonding to hydrophilic tooth tissue may often be poor. Recently, hydrophilic resins have been developed which bond much better to tooth tissue, but they may still bond poorly to gutta percha because of its extremely hydrophobic nature. The result may be a root canal chamber that is not completely sealed, which increases the chance of irritation of the affected area or bacterial contamination, leading to infection and possible failure of the root canal. The level of discomfort and pain associated with an irritated, inflamed, and/or infected root canal area can be great, followed by loss of the tooth.

For the foregoing reasons, there is a need for a root canal filling material and method which is able to provide a better bond and seal between the tooth tissue, any endodontic resin, and the gutta percha cone, giving better protection against irritation and infection than current materials and methods provide. The invention provides an adhesive gutta percha prepared by coating or dipping gutta percha into an adhesive material to yield an adhesive gutta percha that is able to bond to endodontic resins, including hydrophilic resins. The invention also provides related methods for use of the adhesive gutta percha.

BRIEF SUMMARY OF THE INVENTION

The present invention provides an adhesive endodontic cone for placement into a root canal containing an endodontic sealant resin. The adhesive endodontic cone comprises a hydrophobic elastomer substrate that is sized and shaped so as to be at least partially insertable into an exposed root canal of a tooth. The cone also includes an adhesive attached to at least a portion of a surface of the endodontic cone so as to render the cone more chemically compatible with a hydrophilic endodontic resin. The adhesive endodontic cone facilitates complete sealing between the endodontic cone, an endodontic sealant resin, and the hydrophilic tooth tissue of a root canal chamber.

In one embodiment, the adhesive comprises at least one hydrophobic region and at least one hydrophilic region. The hydrophobic region is compatible with the hydrophobic elastomer of the endodontic cone so as to chemically or physically adhere to the hydrophobic elastomer. The hydrophilic region is compatible with a hydrophilic endodontic resin. The adhesive facilitates the formation of a good seal between the hydrophilic tissue of the canal chamber and the endodontic cone.

An example of a hydrophobic region that is compatabile with a hydrophobic elastomer such as gutta percha is polybutadiene, optionally substituted with epoxy groups for added functionality (e.g., where it is desired to employ epoxy adhesive chemistry). In order to bond the hydrophobic polymer comprising the hydrophobic region to the constituents comprising the hydrophilic region, the hydrophobic polymer may be substituted with appropriate functionality (e.g., with hydroxyl groups at one or both ends of the polymer). In one embodiment, a methacrylate (e.g., hydroxyethyl methacrylate) is bonded to one or both ends of the hydrophobic polymer by means of a diisocyanate to yield an adhesive material having at least one diurethane moiety.

In one embodiment, adhesive endodontic cones according to the invention are formed by applying a curable adhesive composition to at least a portion of the surface of an endodontic cone substrate. Because the hydrophobic region is compatible with the hydrophobic material comprising the endodontic cone, the hydrophobic region of the adhesive will tend to orient itself toward the endodontic cone while the hydrophilic region will tend to orient itself away from the endodontic cone, thereby creating a hydrophilic surface on the endodontic cone.

In one embodiment, the curable adhesive is at least partially cured so that it adheres to the hydrophobic elastomer of the endodontic cone, e.g., by physical and/or chemical bonding. Completely curing the adhesive also yields adhesive endodontic cones that resist self-adhesion prior to use. Alternatively, endodontic cones with a partially cured adhesive on a surface thereof can be powder-coated to prevent self-adhesion prior to use.

In practice, the root canal chamber is prepared by removing diseased and surrounding tissue. Once the chamber is prepared, the adhesive endodontic cone is inserted into the chamber. One or more cones may be used as necessary, so as to fill the chamber. An endodontic filling and sealing composition is introduced into the prepared canal, which can then be cured to provide a good seal of the root canal chamber. A hydrophilic composition, such as Endo-REZ, available from Ultradent Products, Inc., may be used, and will bond well to the tooth tissue because of its hydrophilic nature and its ability to penetrate into dentinal tubules. It also bonds well to the inventive endodontic cone. Once the root canal chamber has been filled, the hub of the cone may be removed.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The present invention provides an adhesive endodontic cone for placement into a root canal containing an endodontic sealant resin. The adhesive endodontic cone comprises a hydrophobic elastomer that is sized and shaped so as to be at least partially insertable into an exposed root canal of a tooth. The cone also includes an adhesive attached to at least a portion of a surface of the endodontic cone so as to render the cone more chemically compatible with a hydrophilic endodontic resin. The adhesive endodontic cone facilitates complete sealing between the endodontic cone, an endodontic sealant resin, and the hydrophilic tooth tissue of a root canal chamber.

As used herein, the term "endodontic sealing resin" refers to any endodontic resin used for sealing a root canal chamber. The resin may be hydrophobic or hydrophilic.

As used herein, the term "methacrylate" refers to any methacrylate, while the term "acrylate" refers to any acrylate resin. Hydroxyethylmethacrylate (HEMA) is an example of a methacrylate resin.

II. Adhesive Endodontic Cones

Figure 1:
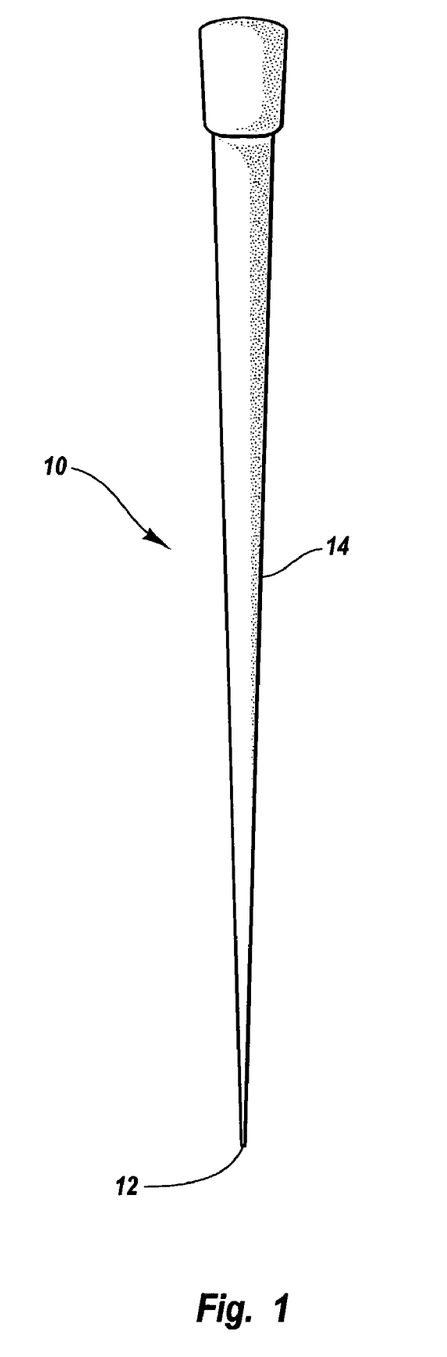
FIG. 1 illustrates an exemplary embodiment of an adhesive endodontic cone.

FIG. 1 is a perspective view of an exemplary adhesive endodontic cone 10 according to the present invention. The endodontic cone 10 is formed of a hydrophobic elastomer substrate that is sized and shaped so as to be at least partially insertable into an exposed root canal. Gutta percha is one example of a hydrophobic elastomer substrate used to form endodontic cones, although other materials such as synthetic rubber, natural rubber, a derivative of natural rubber, silicone rubber, neoprene, isoprene, or polybutadiene may alternatively be used.

As seen in FIG. 1, the endodontic cone 10 includes an insertion tip 12 and an adhesive coating 14 on at least a portion of a surface of the endodontic cone 10. The adhesive 14 renders the cone 10 more chemically compatible with a hydrophilic endodontic resin. An endodontic cone that is more chemically compatible with a hydrophilic endodontic resin facilitates complete sealing between the endodontic cone, an endodontic sealant resin, and the hydrophilic root canal chamber.

The adhesive typically comprises at least one hydrophobic region that chemically or physically adheres to the hydrophobic elastomer, and at least one hydrophilic region that is hydrophilic so as to be more chemically compatible with a hydrophilic endodontic resin. The adhesive coating 14 may be applied as a curable adhesive composition by dipping, brushing, or otherwise coating the endodontic cone 10. The adhesive composition may then be at least partially cured so as to adhere the adhesive to the hydrophobic elastomer of the cone 10.

When initially applied, the curable adhesive composition in one embodiment comprises a carrier, a curing agent (e.g. a chemical or photoinitiator), and a light or chemically curable resin. The carrier may comprise any hydrophobic solvent compatible with the hydrophobic elastomer of the endodontic cone 10. Examples of carriers that may be used within the scope of the invention are benzene, toluene and xylene. The curing agent may comprise any suitable chemical or photoinitiator.

Exemplary curable adhesive compositions according to the invention preferably include one or more a light curable resins in an amount in a range of about 20% to about 80% by weight of the adhesive composition, more preferably in a range of about 30% to about 70% by weight, and most preferably in a range of about 40% to about 60% by weight of the adhesive composition.

Exemplary curable adhesive compositions according to the invention preferably include one or more carrier solvents in an amount in a range of about 20% to about 80% by weight of the adhesive composition, more preferably in a range of about 30% to about 70% by weight, and most preferably in a range of about 40% to about 60% by weight of the adhesive composition.

Exemplary curable adhesive compositions according to the invention preferably include one or more chemical and/or photo curing agents in an amount in a range of about 0.01% to about 5% by weight of the adhesive composition, more preferably in a range of about 0.1% to about 3% by weight, and most preferably in a range of about 0.2% to about 2% by weight of the adhesive composition.

Figure 2:
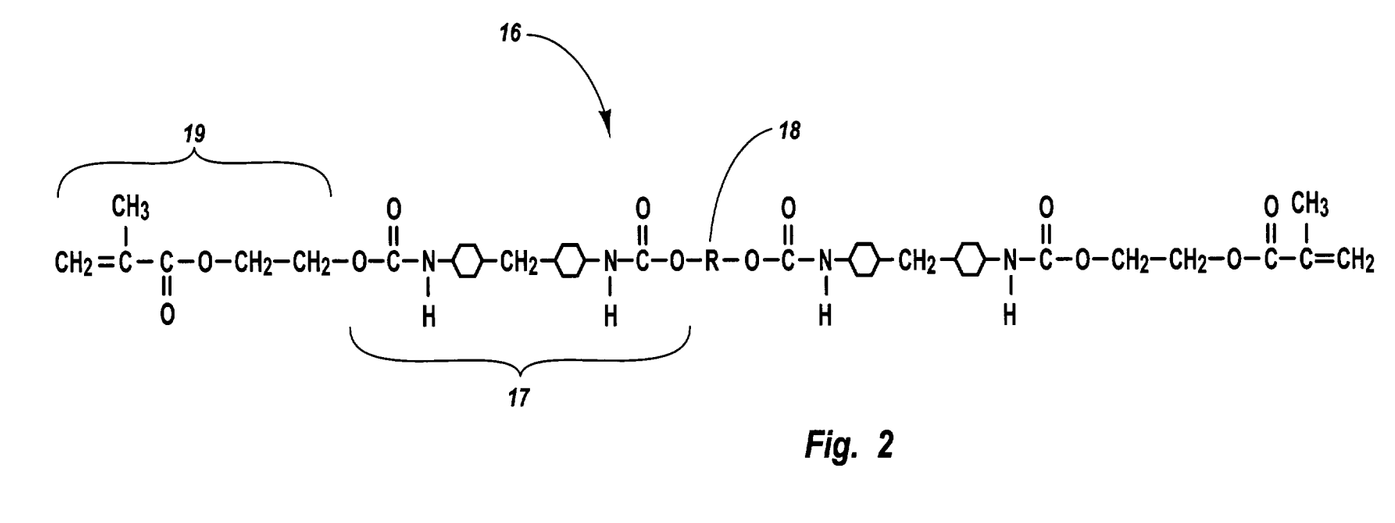
FIG. 2 illustrates the chemical structure of a preferred light curable resin of a curable adhesive composition.

The light curable resin may be any light curable resin that includes a region compatible with the hydrophobic elastomer substrate of the endodontic cone, and that also includes a hydrophilic region that is chemically compatible with a hydrophilic endodontic sealant resin. As illustrated in FIG. 2, one example of a suitable adhesive resin 16 contains a hydrophobic backbone "R" designated as 18, a diurethane constituent 17 on either side of the hydrophobic backbone 18, and a methacrylate constituent 19 attached to each free end of the two diurethane constituents 17. In this embodiment, the configuration of the adhesive composition is:

Methacrylate-Urethane-Hydrophobic Backbone-Urethane-Methacrylate

Nevertheless, it will readily be appreciated that some or all of the adhesive resin may comprise other configurations, examples of which include:

Methacrylate-Urethane-Hydrophobic Backbone and

Methacrylate-Urethane-Hydrophobic Backbone-Urethane-Hydrophobic-Backbone-Urethane-Methacrylate The hydrophobic backbone "R" advantageously comprises one or more hydrophobic polymers or constituents that are chemically compatible with the hydrophobic elastomer of the endodontic cone. In the case where the elastomer comprising the endodontic cone has unsaturated units (e.g., gutta percha), at least a portion of the hydrophobic polymer or constituents comprising the hydrophobic backbone may, in some embodiments, contain ethylenically unsaturated units that are, at least in theory, able to cross link with the unsaturated units within the elastomer comprising the endodontic cone.

In one embodiment, at least a portion of the hydrophobic backbone "R" comprises at least one of polybutadiene or a derivative thereof (e.g., substituted polybutadiene). The individual units comprising the polybutadiene polymer may include cis groups, trans groups, or both. In addition, a portion of the units may comprise vinyl substituted ethylene groups (e.g., where one butadiene molecule reacts with the number 2 carbon of another butadiene molecule instead of the number 4 carbon during polymerization). To provide additional functionality, at least some of the C=C double bonds may be epoxidized to form oxirane units (either cis, trans or both, as well as on at least some of the vinyl groups where present). The hydrophobic backbone may advantageously comprise combinations of one or more of the foregoing constituents.

An example of a hydrophobic polymer suitable for use in forming the hydrophobic backbone of an adhesive composition used to form adhesive endodontic cones according to the invention includes an epoxidized derivative of polybutadiene. One specific example has the following physical properties:

| Epoxy Value (meq/g) | 2–2.5 |
| Epoxy Equivalent weight | 400–500 |
| Oxirane Oxygen (%) | 3.4 |
| Viscosity (mPas @ 300° C.) | 7000 |
| Water (wt % max) | 0.10 |
| Specific Gravity | 1.01 |
| Hydroxyl Value (meq/g) | 1.70 |
| Approximate Microstructure: | |
| Epoxy cis (mol %) | 7–10 |
| Epoxy trans (mol %) | 8–12 |
| Vinyl Double Bonds (mol %) | 22 |
| 1,4-Double Bonds (mol %) | 53–60 |
| Opened Epoxy (mol %) | 2.5 |

Another specific example has the following physical properties:

| Epoxy Value (meq/g) | 3–4 |
| Epoxy Equivalent weight | 260–330 |
| Oxirane Oxygen (%) | 4.8–6.2 |
| Viscosity (mPas @ 300° C.) | 22,000 |
| Water (wt % max) | 0.10 |
| Specific Gravity | 1.01 |
| Hydroxyl Value (meq/g) | 1.70 |
| Approximate Microstructure: | |
| Epoxy cis (mol %) | 7–10 |
| Epoxy trans (mol %) | 8–12 |
| Vinyl Double Bonds (mol %) | 22 |
| 1,4-Double Bonds (mol %) | 53–60 |
| Opened Epoxy (mol %) | 2.5 |

In general, the backbone preferably has a molecular weight of about 500 to 2000 (number average), more preferably about 800 to 1600, and most preferably about 1000 to 1400. In one embodiment, at least a portion of the hydrophobic backbone comprises an epoxidized derivative of polybutadiene having a molecular weight of about 1200 (number average).

The backbone may additionally or alternatively comprise at least one of polyethylene glycol (PEG), polypropylene glycol (PPG), or polyhexatetramethylene-etherglycol (PT-MEG) and derivates thereof.

As seen in FIG. 2, the exemplary compound 16 also contains one or more diurethane constituents 17. The illustrated urethane constituent has the chemical structure:

The illustrated urethane 17 includes cyclohexyl groups separated by a methylene group. Although the illustrated urethane 17 is currently preferred, any of various urethanes containing NHCOO linkages may be used (e.g., separated by one or more linear alkyl groups and/or one or more aryl groups, such as phenyl).

As seen in FIG. 2, the exemplary compound also contains one or more methacrylate constituents 19. The illustrated methacrylate has the chemical structure:

The illustrated methacrylate constituents 19 are each located adjacent to a respective urethane constituent 17 and form the terminal ends of the adhesive resin 16. Methacrylate constituent 19 is an example of a hydrophilic constituent that is compatible with a hydrophilic endodontic sealant resin. Any methacrylate or acrylate may be used as a methacrylate constituent 19 in the compound 16.

The compound illustrated in FIG. 2 is exemplary only. Any compound containing at least one hydrophobic region (e.g., a hydrophobic polymer chain) that is able to adhere to the hydrophobic elastomer of the endodontic cone 10, and also that contains at least one hydrophilic region (e.g., a methacrylate or acrylate bonded to the hydrophobic region by means of a diurethane constituent) that is chemically compatible with a hydrophilic endodontic sealant resin may alternatively be used.

In one embodiment, the adhesive coating is applied to the endodontic cone by dipping, brushing, or by any other suitable method of applying a coating to a substrate. The adhesive is at least partially cured so as to cause the adhesive to adhere to the hydrophobic elastomer of the endodontic cone.

Depending on the degree of curing achieved, there may be an inhibition layer present after curing. Such a layer may cause individual adhesive endodontic cones to adhere to adjacent cones prior to use and during storage. The presence of oxygen inhibits curing of some resins, particularly at the surface next to the oxygen. In order to inhibit adhesion of one endodontic cone to another during storage and prior to use, the adhesive coating may be cured under a non-oxygen gas (e.g., nitrogen). Alternatively, a powder coating, such as a silicon oxide, fumed silica, talc, calcium carbonate, zinc oxide, or titanium oxide may be applied to inhibit adhesion of one endodontic cone to another during storage and prior to use (e.g., insertion of one or more cones into a root canal).

III. Method of Making an Exemplary Light Curable Adhesive Resin

As discussed above, exemplary adhesive resins contain a hydrophobic backbone, at least one diurethane constituent, and at least one methacrylate constituent. These are advantageously joined together in a multi-step process.

In one embodiment, a resin or polymer suitable for making the hydrophobic backbone is obtained so as to have one or more hydroxyl groups (e.g., two terminal hydroxyl groups at either end of a linear polymer and/or one or more hydroxyl groups within the interior of the polymer). This polymer is reacted with a suitable diisocyanate under known conditions to yield an intermediate compound having a urethane linkage between at least one side or portion of the hydrophobic polymer and a remaining reactive isocyanate group. In one embodiment, the backbone resin or polymer is reacted with a diisocyanate having the following chemical structure:

The reaction may proceed between the hydroxyl group of the backbone and one of the isocyanate groups of the diisocyanate. Attaching the backbone and diisocyanate results in an intermediate compound having an exemplary chemical structure such as:

The intermediate compound may be reacted with an acrylate or methacrylate substituted with a hydroxyl group, e.g., HEMA, which has the following chemical structure:

The hydroxyl group of the methacrylate reacts with the remaining isocyanate group of the intermediate compound. The resulting compound includes a hydrophobic portion (i.e. the backbone) and a hydrophilic portion (i.e. methacrylate) having an exemplary chemical structure such as:

in FIG. 2. The synthesized compounds may be isolated and separated from products resulting from side reactions, or the resulting compound(s) may be used without further refinement or isolation as a light curable compound.

IV. Methods of Using the Inventive Endodontic Cones

Figure 3:
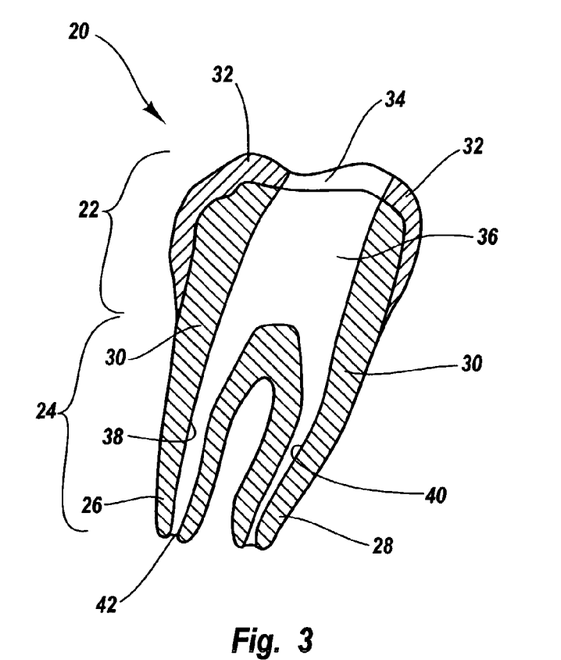
FIG. 3 illustrates an endodontically prepared root canal chamber of a diseased tooth.

An exemplary method of using the adhesive endodontic cones according to the invention will now be described. FIG. 3 shows a cross-sectional view of a tooth that has been endodontically prepared. The tooth is generally designated by the numeral 20. It has a crown portion 22 and a root portion 24 made up of first and second roots 26 and 28. The tooth is composed of dentin material 30 with the crown 22 being covered by enamel 32.

In FIG. 3, a portion of the enamel and dentin have been removed from the crown 22 (e.g., by drilling) to form an access opening 34 providing access to the interior 36 of the crown. The pulp material originally present within the crown interior 36 and root canals 38 and 40 has been removed by conventional endodontic procedures (e.g., using one or more endodontic files). The root canals 38 and 40 have been endodontically prepared by procedures known in the art. Each root canal terminates at an apex 42, which is a small opening through which the nerve tissue originally entered the tooth.

Figure 4:
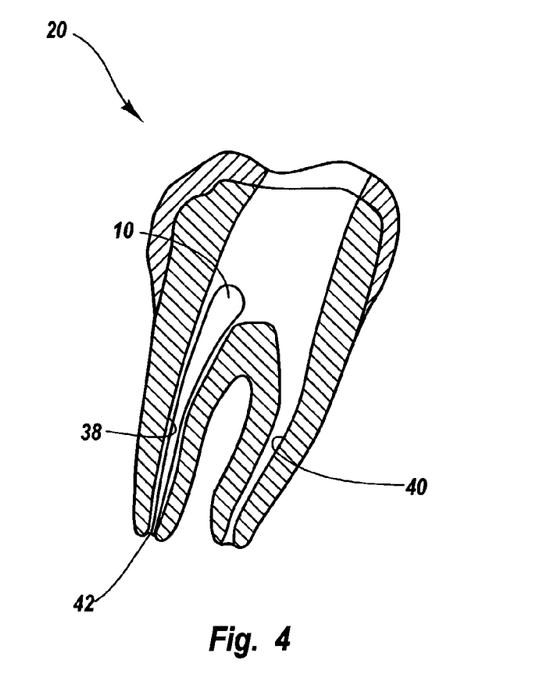
FIG. 4 illustrates an adhesive endodontic cone inserted in the root canal chamber.

Referring to FIG. 4, the adhesive endodontic cone 10 is inserted in the prepared root canal 38 of tooth 20 and is pushed into the canal 38 starting at insertion tip 12 until fully inserted so as to fill apex 42. One or more adhesive endodontic cones 10 may be inserted into the root canal as required to fill the root canal chamber. If multiple cones are used, they may be packed down into the desired position. Root canal 40 is filled with an adhesive endodontic cone 10 in the same way as root canal 38.

Figure 5:
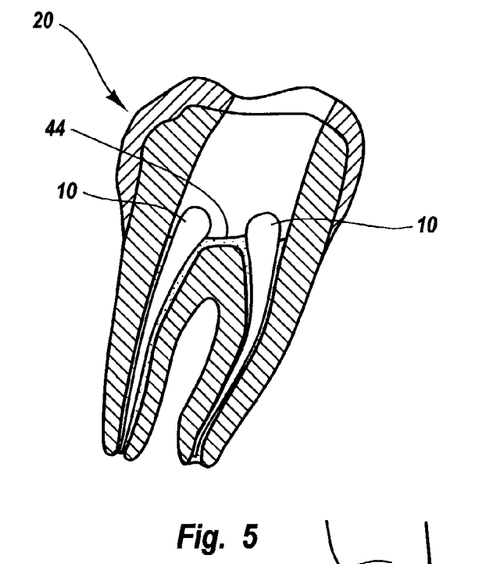
FIG. 5 illustrates an endodontic filling and sealing composition introduced into the prepared root canal.

Referring to FIG. 5, an endodontic filling and sealing composition 44 is used to fill any spaces between the endodontic cone 10 and the sides of root canal chambers 38 and 40. The endodontic filling and sealing composition 44 may be introduced into the root canal chamber before, after, or simultaneously with the adhesive endodontic cone 10.

A hydrophilic resin, such as Endo-REZ, available from Ultradent Products, Inc., is preferred because of its ability to penetrate into the hydrophilic dentinal tubules and side canals of the chamber, facilitating a strong and complete seal between the hydrophilic tissue of the chamber and the adhesive endodontic cone. A variety of suitable endodontic resins suitable for use with the inventive endodontic cones are disclosed in U.S. Pat. No. 6,500,004; U.S. application Ser. No. 10/121,389, filed Apr. 12, 2002; and U.S. application Ser. No. 10/128,970, filed Apr. 23, 2002. For purposes of disclosing endodontic sealing compositions, the foregoing patent and applications are incorporated by reference. Because of the depth of the root canal, it is preferable that endodontic composition 44 be a chemical cure resin, It will be noted that the compound set forth above is merely exemplary. It will also be noted that the backbone used in the synthesis may include two hydroxyl groups, which would result in a compound such as the one illustrated although a light curable resin could alternatively be used with appropriate care. Endo-REZ is a suitable two-part chemical cure resin comprising a hydrophilic resin and a chemical curing agent that may be used to seal the area between the canal surface and the adhesive endodontic cone 10. A dual cure Endo-REZ may also be used, which can be light cured to accelerate the time when a filling material may be placed over the filled root canal.

Figure 6:
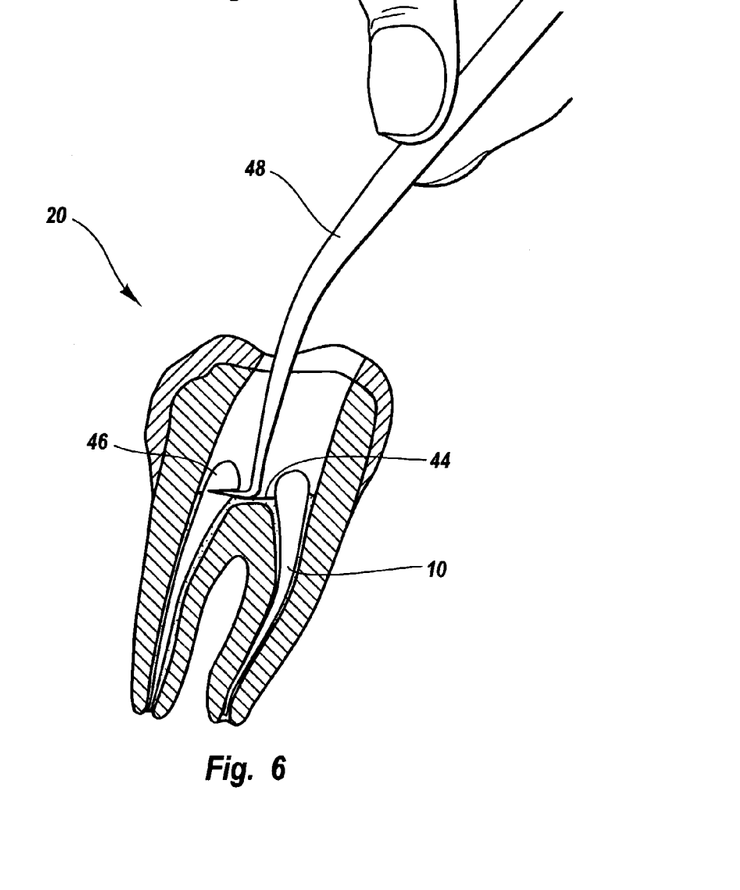
FIG. 6 illustrates removal of the hub of the adhesive endodontic cone.

As illustrated in FIG. 6, once sufficiently cured, the hub 46 of the adhesive endodontic cone 10 may then be removed by instrument 48 so as to form a uniform, smooth surface. The filled root canal chamber is now ready for further treatment, such as placement of a post, a crown, a composite resin or other procedures known in the art.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An adhesive endodontic cone for placement into a root canal containing an endodontic sealant resin, the adhesive endodontic cone comprising:
    an endodontic cone comprising a hydrophobic elastomer and that is sized and shaped so as to be at least partially insertable into an exposed root canal of a tooth; and
    an adhesive attached to at least a portion of a surface of the endodontic cone so as to render the endodontic cone more chemically compatible with a hydrophilic endodontic resin,
        wherein the adhesive comprises a hydrophobic portion adhered to the hydrophobic elastomer of the endodontic cone and a hydrophilic portion that is chemically compatible with the hydrophilic endodontic resin.

2. An adhesive endodontic cone as recited in claim 1, wherein the hydrophobic elastomer comprises gutta percha.

3. An adhesive endodontic cone as recited in claim 1, wherein the hydrophobic elastomer comprises at least one of synthetic rubber, natural rubber, a derivative of natural rubber, silicone rubber, neoprene, isoprene, or polybutadiene.

4. An adhesive endodontic cone as recited in claim 1, wherein the adhesive is formed by applying to the surface of the endodontic cone a curable adhesive composition that is then at least partially cured so as to adhere hydrophobic portion of the adhesive to the hydrophobic elastomer of the endodontic cone.

5. An adhesive endodontic cone as recited in claim 4, wherein the curable adhesive composition, when initially applied to the surface of the endodontic cone, comprises a light curable resin, a photoinitiator, and a carrier.

6. An adhesive endodontic cone as recited in claim 5, wherein the light curable resin comprises at least one hydrophobic backbone that is chemically compatible with the hydrophobic elastomer of the endodontic cone, at least one urethane constituent on at least one side of the backbone, and at least one methacrylate constituent adjacent to the urethane constituent.

7. An adhesive endodontic cone as recited in claim 6, wherein the backbone comprises a hydrophobic polymer chain.

8. An adhesive endodontic cone as recited in claim 7, wherein the hydrophobic polymer chain comprises polybutadiene or a derivative thereof.

9. An adhesive endodontic cone as recited in claim 7, wherein the hydrophobic polymer chain comprises at least one of polybutadiene, polyethylene glycol, polypropylene glycol, or polyhexatetramethyleneetherglycol.

10. An adhesive endodontic cone as recited in claim 7, wherein the hydrophobic polymer chain comprises C=C double bonds in at least one of cis or trans configurations.

11. An adhesive endodontic cone as recited in claim 10, wherein at least some of the C=C double bonds have been epoxidized to form oxirane units.

12. An adhesive endodontic cone as recited in claim 11, wherein the hydrophobic polymer chain comprises at least one vinyl substituted ethylene group.

13. An adhesive endodontic cone as recited in claim 1, further comprising a powder coating on the adhesive to inhibit adhesion of one endodontic cone to another endodontic cone prior to insertion of one or both endodontic cones into a root canal.

14. An adhesive endodontic cone as recited in claim 13, wherein the powder coating comprises at least one of silicon oxide, fumed silica, talc, calcium carbonate, zinc oxide, or titanium oxide.

15. An adhesive endodontic cone for placement into a root canal containing an endodontic sealant resin, the adhesive endodontic cone comprising:
    an endodontic cone substrate comprising a hydrophobic elastomer and that is sized and shaped so as to be at least partially insertable into an exposed root canal of a tooth; and
    an adhesive attached to at least a portion of a surface of the endodontic cone substrate so as to render the endodontic cone more chemically compatible with a hydrophilic endodontic resin, the adhesive attached to the endodontic cone substrate formed by:
        applying a curable adhesive composition to at least a portion of the surface of the endodontic cone substrate; and
        at least partially curing the curable adhesive composition so that a portion of the adhesive composition chemically adheres to the hydrophobic elastomer of the endodontic cone substrate and another portion of the adhesive composition is chemically bondable to the hydrophilic endodontic resin.

16. An adhesive endodontic cone as recited in claim 15, wherein the curable adhesive composition, when applied to the surface of the endodontic cone, comprises a light curable resin, a photoinitiator, and a carrier.

17. An adhesive endodontic cone as recited in claim 16, wherein the light curable resin comprises at least one backbone that is chemically reactive with the hydrophobic elastomer of the endodontic cone, at least one urethane constituent on either side of the backbone, and at least one methacrylate constituent adjacent to the urethane constituent.

18. An adhesive endodontic cone as recited in claim 17, wherein the backbone comprises a hydrophobic polymer chain.

19. An adhesive endodontic cone as recited in claim 18, wherein the hydrophobic polymer chain comprises epoxidized polybutadiene.

20. An adhesive endodontic cone as recited in claim 16, wherein the carrier comprises toluene.

21. An adhesive endodontic cone as recited in claim 16, wherein the light curable resin comprises about 20% to about 80% by weight of the curable adhesive composition.

22. An adhesive endodontic cone as recited in claim 16, wherein the light curable resin comprises about 30% to about 70% by weight of the curable adhesive composition.

23. An adhesive endodontic cone as recited in claim 16, wherein the light curable resin comprises about 40% to about 60% by weight of the curable adhesive composition.

24. An adhesive endodontic cone as recited in claim 15, wherein the curable adhesive composition is cured under a non-oxygen gas so as to at least partially prevent formation of an inhibition layer.

25. An adhesive endodontic cone as recited in claim 24, wherein said non-oxygen gas comprises nitrogen.

26. An adhesive endodontic cone as recited in claim 15, further comprising a powder coating on the adhesive to inhibit adhesion of one endodontic cone to another endodontic cone prior to insertion of one or both endodontic cones into a root canal.

27. An adhesive endodontic cone for placement into a root canal containing an endodontic sealant resin, the adhesive endodontic cone comprising:
   an endodontic cone comprising a hydrophobic elastomer and that is sized and shaped so as to be at least partially insertable into an exposed root canal of a tooth; and
   an adhesive resin attached to at least a portion of a surface of the endodontic cone so as to render the endodontic cone more chemically compatible with a hydrophilic endodontic resin, the adhesive resin comprising a hydrophobic backbone that is chemically compatible with the hydrophobic elastomer of the endodontic cone, at least one urethane constituent on at least one side of the backbone, and at least one methacrylate constituent adjacent to the urethane constituent.

28. An adhesive endodontic cone as recited in claim 27, wherein the backbone comprises a hydrophobic polymer chain.

29. An adhesive endodontic cone as recited in claim 28, wherein the hydrophobic polymer chain comprises polybutadiene or a derivative thereof.

30. An adhesive endodontic cone as recited in claim 28, wherein the hydrophobic polymer chain comprises at least one of polyethylene glycol, polypropylene glycol, or polyhexatetramethyleneetherglycol.

31. An adhesive endodontic cone as recited in claim 28, wherein the hydrophobic polymer chain comprises C=C double bonds in at least one of cis or trans configurations.

32. An adhesive endodontic cone as recited in claim 31, wherein at least some of the C=C double bonds have been epoxidized to form oxirane units.

33. An adhesive endodontic cone as recited in claim 28, wherein the hydrophobic polymer chain comprises at least one vinyl substituted ethylene group.

* * * * *

UNITED STATES PATENT AND TRADEMARK OFFICE
CERTIFICATE OF CORRECTION

| | | |
|---|---|---|
| PATENT NO. | : 6,986,662 B2 | Page 1 of 1 |
| APPLICATION NO. | : 10/410310 | |
| DATED | : January 17, 2006 | |
| INVENTOR(S) | : Erich Haschke | |

It is certified that error appears in the above-identified patent and that said Letters Patent is hereby corrected as shown below:

<u>Column 9</u>
Line 46, after "adhere" insert --the--

<u>Column 10</u>
Line 9, change "claim 11" to --claim 10--

Signed and Sealed this

Twenty-second Day of August, 2006

JON W. DUDAS
*Director of the United States Patent and Trademark Office*